United States Patent [19]

Higa

[11] Patent Number: 4,627,817

[45] Date of Patent: Dec. 9, 1986

[54] DENTAL BRIDGE REMOVER

[76] Inventor: Jack Higa, 925 Esquimalt, West Vancouver, British Columbia, Canada, V7T 1J8

[21] Appl. No.: 711,987

[22] Filed: Mar. 14, 1985

[30] Foreign Application Priority Data

Mar. 20, 1984 [CA] Canada .................................. 449953

[51] Int. Cl.[4] .............................................. A61C 3/00
[52] U.S. Cl. ................................................. 433/152
[58] Field of Search ............... 433/154, 155, 161, 153, 433/152

[56] References Cited

U.S. PATENT DOCUMENTS 2,210,349  8/1940  Van Beeck ........................... 433/152
4,417,876  11/1983  Lynch .................................. 433/161

*Primary Examiner*—Robert Peshock
*Attorney, Agent, or Firm*—Klarquist, Sparkman, Campbell, Leigh & Whinston

[57] ABSTRACT

An instrument for removing dental bridgework is disclosed. The instrument includes a support beam for extending into a patient's mouth over bridgework bonded therein; one or more bracing pins; and pulling means for drawings a pulling cord or cords looped beneath the bridgework in an occlusal direction towards the beam. In one structure, the bracing pin or pins have lower ends receivable by a hole or holes cut in the occlusal surface of a retainer or retainers forming part of the bridgework. In another structure, the lower end of a bracing pin has a protective footing for bracing against the exposed cusp of a tooth.

32 Claims, 12 Drawing Figures

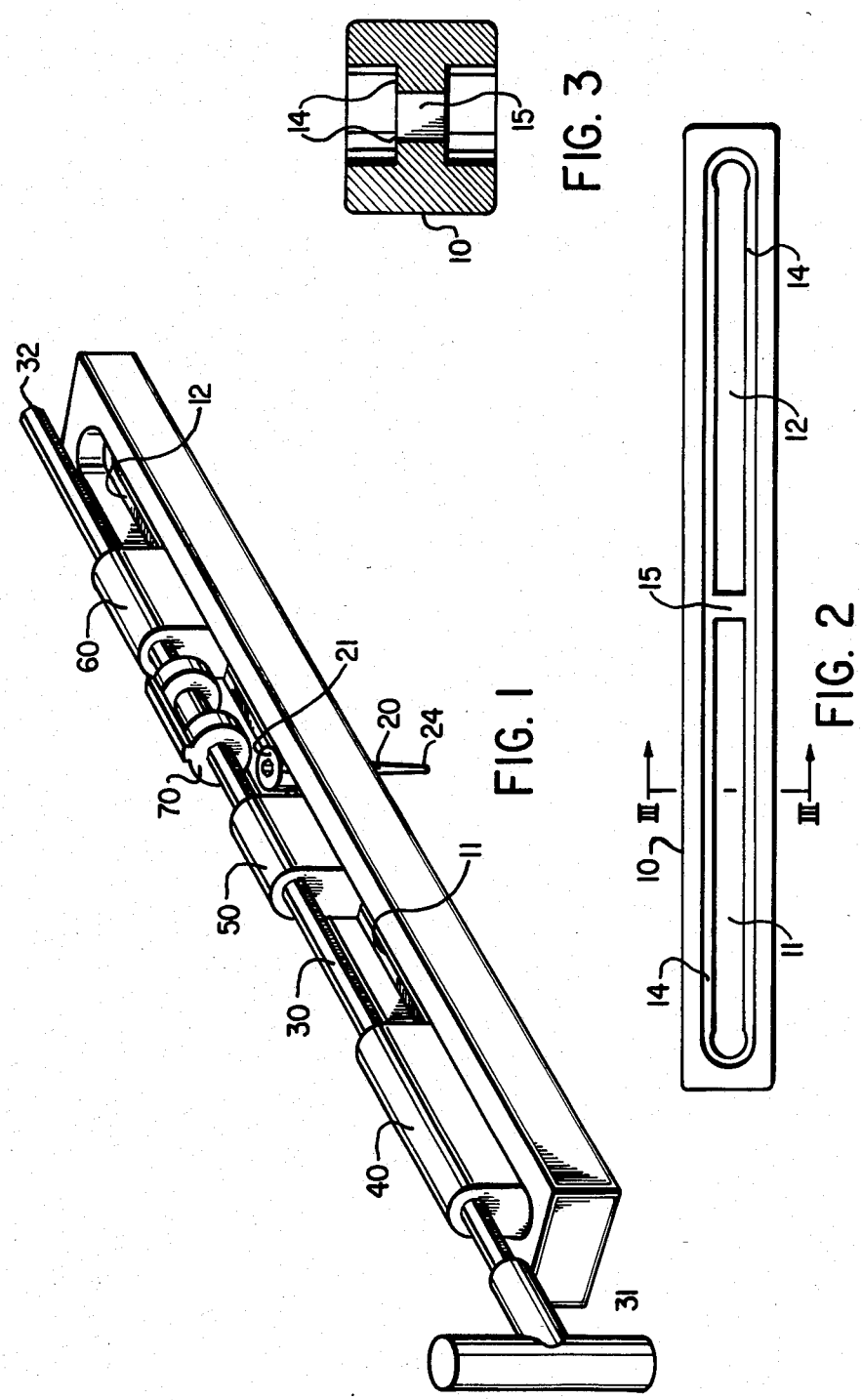

DENTAL BRIDGE REMOVER

FIELD OF THE INVENTION

This invention relates to the field of dentistry, and in particular to instrumentation used for the removal of dental bridgework.

BACKGROUND OF THE INVENTION

Fixed bridgework which has been meticulously crafted and which conforms to well known functional principles can fail for various reasons. Not even the most skillful operators can avoid an occasional failure regardless of the care extended and the consideration given to anticipated problems. When failures occur, they are a source of both consternation and frustration. For example, a soldered joint may fail thereby jeopardizing the utility and value of an entire dental bridge. The resulting cost of correcting the problem must be measured not only in monetary terms but also in terms of trauma to the dental patient, and the time involved for all parties concerned.

When it becomes necessary to remove a well placed dental bridge, the task of removing the prosthesis intact can be extremely difficult. Past methods can be destructive to the prosthesis and have often resulted in the deformation of metal and/or the chipping of porcelain. Furthermore, excessive stress can be placed on the periodontium thereby resulting in some injury to the dental patient. In cases, for example, where two abutments are involved, the dentist is often forced to cut the retainers.

A primary object of the present invention is to provide a new and improved instrument which assists to avoid or at least minimize such problems heretofore associated with the removal of dental bridgework, and which simplifies and eases the process of such removal for both the dentist and his patient.

A further object of the present invention is to provide an instrument for the removal of dental bridgework which may be used to remove a variety of dental bridge configurations.

SUMMARY OF THE INVENTION

To these ends, and in accordance with a broad aspect of the present invention, there is provided an instrument for removing dental bridgework which comprises a support beam having a sufficient longitudinal extension to extend into a patient's mouth over bridgework which is bonded therein, a bracing pin having an upper end mounted to the beam, and pulling means supported by the beam for rotatably engaging and drawing a pulling cord looped beneath the bridgework in an occlusal direction towards the beam to break the bond when the beam is braced by the pin.

In one embodiment, the bracing pin has a lower end receivable by a receiving hole cut in the occlusal surface of a retainer of the bridgework, In another embodiment, a lower end of the bracing pin has a protective footing for bracing against the exposed cusp of a tooth. As will be seen, the latter embodiment is considered particularly useful for removal of dental bridgework known as a "Maryland Bridge". Advantageously, the protective footing is a detachable element which may be fitted over the lower end of the bracing pin referred to above.

As will become apparent, it is contemplated that the instrument may require two bracing pins for some applications. However, whether one or two bracing pins are present, their upper ends are preferably mounted to the support beam in a releasable manner which enables the pin or pins to be positioned at selected locations along the beam.

Various possible materials may be used for a pulling cord (single and sometimes double stranded 0.020 inch dead soft orthodontic ligature wire has been found to work well), and various possible pulling means may be used to draw the pulling cord. In a preferred embodiment, such pulling means comprises an elongated rotatable shaft which enables the cord to be drawn by a reeling action as the shaft is rotated. When sufficient tension is achieved in the cord, the bonding of the bridge separates. A reeling spool may be mounted on the shaft to enable the pulling means to achieve a better grip on the cord. The spool is slideably mounted on the shaft to permit the spool to be positioned at a selected location along the shaft. Alternately, a plurality of spaced apart holes or an elongated slot may be provided in the shaft for receiving and engaging a pulling cord.

Preferably, the shaft itself is rotatably supported by main and secondary bearing supports mounted on the beam, and, as in the case of bracing pins, it is considered desirable to mount such supports in a releasable manner which permits positioning of the supports at selected locations along the beam.

The overall construction of the present invention is not complicated, and it has been found to provide an effective and efficient means for removing failed dental bridgework. It serves to simplify and foreshorten the process of removing dental bridgework, and should thereby tend to reduce the cost of the work done. Although it has been found to work best on posterior bridgework, it can also be used on anterior bridgework.

Notwithstanding the fact that considerable force is applied by the instrument, and apart from the small occlusal openings required to receive bracing pins (which openings can be easily filled with solder), experience to date with the instrument of the present invention has shown that there is less likelihood of scarring or deformation to the bridge provided that the bridge is well constructed.

The present invention also serves to minimize the risk of physical pain or injury to the patient. It has been found that most patients can easily tolerate the effects of using the instrument of the present invention, and that the use of anaesthetics may often be avoided. This arises through an overall balancing of forces which are at work during use of the invention. When used properly, there are no lateral forces directed to the periodontium. Thus, the periodontal ligament of the patient's retainer tooth is protected.

The overall ease and facility with which the instrument can be used, coupled often with the absence of anaesthetic procedures, all serves to minimize any mental or physical discomfort or trauma for the dental patient.

The foregoing and other features of the invention will now be described in more detail with reference to the drawings.

BRIEF DESCRIPTION OF THE DRAWINGS

FIG. 1 is a perspective view of an instrument for removing dental bridgework embodied by the present invention.

FIG. 2 is a top elevation view of the beam shown in FIG. 1.

FIG. 3 is a section view of the beam taken along line 3—3 in FIG. 2.

DESCRIPTION OF THE PREFERRED EMBODIMENT

Figure 4:
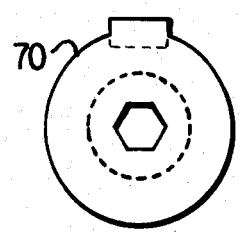
FIG. 4 is an end elevation view of the reeling spool shown in FIG. 1.

The dental bridge removing instrument shown in FIGS. 1 to 8 generally comprises a support beam 10; a bracing pin 20; an elongated rotatable shaft 30; a main support 40 and secondary supports 50, 60; and a reeling spool 70. Although only one bracing pin 20 is shown in FIGS. 1 to 8, it is to be understood that the use of two bracing pins is contemplated for some applications.

Various materials may be used for the construction of such components, stainless steel being considered exemplary because it is strong, anti-corrosive, and easy to sterilize. Since the instrument is used in a patient's mouth, the use of sharp edges or corners which may cause injury is avoided in the overall design of the instrument.

As is best illustrated in FIGS. 2 and 3, beam 10 has elongated openings 11, 12 disposed along the longitudinal extension of the beam, the perimeter of such openings being defined by a flange 14 forming part of the beam. Flange 14 includes a relatively small bridge segment 15 which physically separates opening 11 from opening 12, but the real purpose is to provide added mechanical strength to the beam. Segment 15 is not considered imperative for the embodiment shown and, in its absence, openings 11 and 12 would obviously form a single elongated opening.

Figure 6:
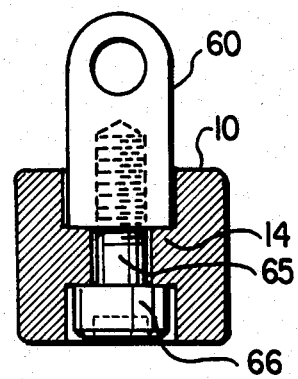
FIG. 6 is an end elevation view of one of the bearing supports shown in FIG. 1.
Figure 7:
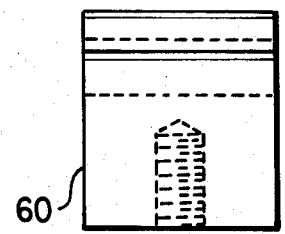
FIG. 7 is a side elevation view of one of the bearing supports shown in FIG. 1.

Openings 11 and 12 and flange 14 facilitate a number of purposes. Firstly, as will be described in more detail hereinafter, the openings provide space through which a pulling cord or cords may be extended from bridgework that is to be removed. Secondly, as is best illustrated by FIG. 6, openings 11 and 12 together with flange 14 enable a simple mechanism for mounting supports 40, 50 and 60 to the beam. (Although only support 60 and opening 12 is depicted in FIG. 6, the mounting mechanism is generally the same for all supports.) Thirdly, as is best illustrated by FIG. 8, openings 12 (shown) or 11 (not shown), together with flange 14 likewise enable a simple mechanism for mounting a bracing pin 20 to the beam.

Figure 8:
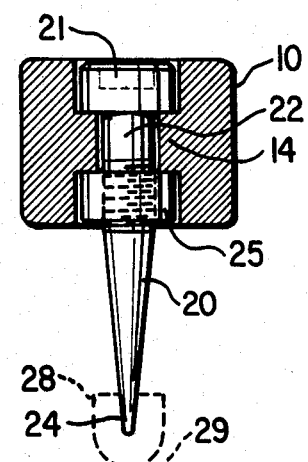
FIG. 8 is an elevation view of the bracing pin shown in FIG. 1.

In more detail with reference to FIG. 8, it can be seen that pin 20 has an upper end which includes a head 21 and a threaded portion 22, the latter of which threadingly engages a retaining nut 25. The lower side of head 21 normally engages the top of flange 14, and the upper side of nut 25 normally engages the bottom of flange 14. Nut 25 is elongated so that it cannot turn in the channel of beam 10 formed below flange 14. This permits pin 20 to be threaded into the nut and tightly mounted at a selected position on the beam. If it is desired to move pin 20, the pin may be released or slightly loosened from nut 25 as if the pin was a screw. This permits sliding moving of pin 20 (including nut 25) along the longitudinal extension of beam 10 from one selected position to another while the pin remains loosely mounted to beam 10. Of course, bridge segment 15 of flange 14 will preclude such sliding movement along the full extent of the beam's longitudinal extension. If it became desirable to move pin 20 from the area of opening 12 to the area of opening 11, it would be necessary to completely separate the pin from its retaining nut 25.

Bracing pin 20 has a lower end 24 which is adapted to be received by a receiving hole cut in the occlusal surface of a retainer (not shown in FIGS. 1 to 8) of bridgework to be removed. The pin tapers towards lower end 24 so as to minimize the size of the receiving hole. Element 28 shown in broken outline in FIG. 8 only of FIGS. 1 to 8, is a detachable protective footing to be used in cases where it is desired to brace the pin against the exposed cusp of a tooth, as opposed to having the pin inserted into a receiving hole cut in the occlusal surface of a retainer. Footing 28 is circular in cross-section with a rounded tip 29. Suitable materials include rubber, plastic or the like having a centrally disposed top hole into which lower end 24 of pin 20 may be tightly (but removably) inserted. The use of rubber, plastic or the like is designed to avoid scratching or injury to the tooth surface.

In more detail with reference to FIG. 6, it can be seen that support 60 normally rests on top of flange 14 in the channel of beam 10 formed above the flange. Support 60 may be secured in such position by tightening screw 65, the head 66 of which will engage the bottom of flange 14 in the tightened condition. If it is desired to move support 60, screw 65 may be loosened or released to a degree which holds the support loosely mounted to the beam yet permits sliding movement of the support along the longitudinal extension of the beam from one selected position to another. However, as in the case of the pin 20, bridge segment 15 of flange 14 will preclude such sliding movement along the full extent of the beam's longitudinal extension. Thus, if it became desirable to move support 60 from the area of opening 12 to the area of opening 11, it would be necessary to remove screw 65 altogether.

As indicated above, supports 40 and 50 are mounted to beam 10 in like manner as support 60. However, in the case of support 40, this similarity is basically for the purpose of having uniformity in the mounting mechanisms used. It is not especially intended to facilitate sliding movement of support 40, it being appreciated that support 40 is a main support which will usually be positioned at the end of beam 10 as shown in FIG. 1. In contrast, secondary supports 50, 60 may be situated at various positions on beam 10 depending on the requirements of the particular job at hand. Supports 40, 50 and 60 all serve to rotatably support shaft 30 which extends longitudinally through each of the supports in parallel relation with beam 10. As can be seen in FIG. 1, a handle or grip 31 is provided at one end of shaft 30, the purpose being to better enable a manual rotational force to be applied to the shaft.

Supports 40, 50 and 60 permit free rotational movement of shaft 30. Further, they offer no resistance to longitudinal movement of shaft 30 in supports. In other words, shaft 30 may be freely inserted through the supports to the position shown in FIG. 1. Likewise, shaft 30 may be freely withdrawn from the position shown in FIG. 1 so as to completely separate the shaft from the remaining portion of the instrument.

The openings through which shaft 30 extends in supports 40, 50 and 60 are circular in cross-section. However, the cross-section of the shaft from tip 32 to grip 31 is hexagonal. One reason for such hexagonal cross section is to enable non-rotational mounting of reeling spool 70 on the shaft. A further reason is to enable the shaft to be used as a screwdriver to tighten (or loosen) the screws (such as screw 65) used to mount supports 40, 50 and 60 to beam 10, and also to tighten (or loosen) bracing pin 20 at a given location on the beam. To accommodate the use of shaft 30 as a screwdriver, the heads of the screws used to mount the supports to beam 10 (such as head 66 of screw 65) and head 21 of bracing pin 20 each have an hexagonal recess in their top to receive and engage hexagonal tip 32 of shaft 30 (viz. the screws and the bracing pin each have a head not unlike the head of an hexagonal Allen-head screw, and shaft 30 including grip 31 may be used like an hexagonal Allen-head screwdriver.)

Reeling spool 70 is slidably mounted on shaft 30 in a manner which permits the spool to slide along the shaft between supports. However, as noted above and as can be seen from FIG. 4, the spool cannot rotate relative to the shaft. The opening in the spool through which shaft 30 extends has an hexagonal cross-section cooperative with the hexagonal cross-section of the shaft to prevent such rotation.

Shaft 30 with grip 31 and reeling spool 70 together comprise a pulling means for drawing a pulling cord (not shown in FIGS. 1 to 8) towards beam 10. As described below in more detail, such cord is normally looped beneath bridgework to be removed and is strung in an occlusal direction through opening 11 or 12 in beam 10 to the pulling means—and in particular to spool 70 thereof. Spool 70 includes a slot opening 74 for receiving and gripping the cord.

Figure 5:
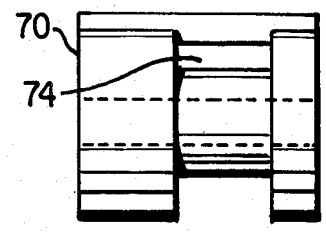
FIG. 5 is a side elevation view of the reeling spool shown in FIG. 1.

The use of reeling spool 70 as depicted in FIGS. 1, 4 and 5 is considered desirable because it is relatively easy to thread and engage a pulling cord onto the spool in a manner which reduces the possibility of slippage when the cord is placed under tension. However, other arrangements are possible. For example, a plurality of spaced apart holes for receiving the cord may be drilled or punched in shaft 30 transverse to the longitudinal extension of the shaft. Alternately, it would be possible to provide a slotted opening or openings along the length of shaft 30 for the purpose of engaging one or more pulling cords. However, such arrangements would lose the advantage of using a commonly available solid structural element such as shaft 30.

There is no absolute criticality to the dimensions of the instrument shown in FIG. 1. However, to give a better perspective on the dimensions generally involved, it may be noted that an instrument generally as described has been made and found to work well having overall beam dimensions of about 9 cm (length) by 8 mm (width) by 8 mm (height). Flange 14 of the beam had an inward width of about 1 mm leaving apertures 11 and 12 each with a width of about 2 mm. Apertures 11 and 12 extended to within about 2 mm of the utmost ends of beam 10. The vertical thickness of flange 14 was about 2 mm, and the width of bridge segment 15 (lengthwise of beam 10) was also about 2 mm. Shaft 30 had a standard 3/32" (inch) cross-section. The heads of all mounting screws (such as head 66 of screw 65), the head 21 of pin 20, and spool 70 were all adapted to snugly accomodate such cross-section. Supports 40, 50 and 60 each had a height of about 11 mm; the length of support 40 being about 14 mm, and the length of supports 50 and 60 each being about 7 mm. Main support 40 was given a length double that of secondary support 50, 60 in order to provide improved mechanical support for shaft 30 at the end of the shaft where operating forces are applied. Spool 70 had an overall length of about 1 cm and an outer diameter of about 7.8 mm. The length of slot opening 74 in spool 70 was about 4 cm running from about 4 cm from one end of the spool to within about 2 mm of the opposite end. The spool diameter below slot 74 was about 3.5 mm and the vertical clearance of the slot was about 1.5 mm. Pin 20 from its upper end immediately below head 21 to the tip of lower end 24 had a length of about 1.5 cm. The instrument when assembled in the manner shown in FIG. 1 could conveniently extend and fit into a patient's mouth.

Having described the structure of the instrument shown in FIGS. 1 to 8, its use will now be described with reference to three examples. In the first example two bracing pins 20 are used. In the third example, which also depicts a variant structure 30' of shaft 30, one bracing pin is again used—but the pin includes a protective footing.

CASE 1

Figure 9A:
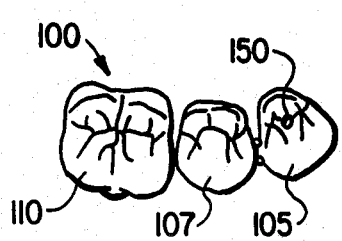
FIGS. 9A to 9D depict dental bridgework and an example of the use of the instrument shown in FIG. 1.

This example, illustrated by FIGS. 9A to 9D, takes a case where a dental bridge generally designated 100 has one retainer 105 tightly cemented and one crown 110 which is loose. A pontic 107 is disposed therebetween. In removing such bridgework for purposes of repair, the following steps may be followed:

STEP 1: As shown in FIG. 9A, a small hole 150 is cut into the occlusal surface of retainer 105. The occlusal surface of the preparation is sufficiently exposed to just receive lower end 24 of a bracing pin 20. During this procedure, there should be no binding of the metal at any time.

Figure 9B:
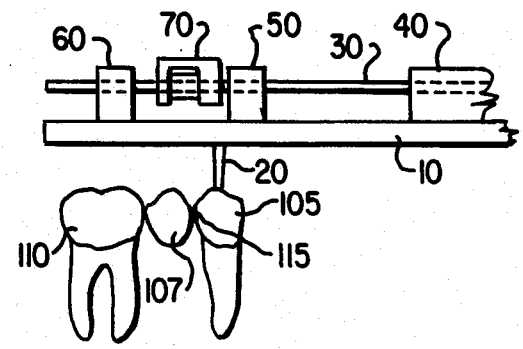

STEP 2: For purposes of establishing and setting the position of adjustable components, the instrument of FIG. 1 is placed in the patient's mouth generally as shown in FIG. 9B. Pin 20 is set to extend down to retainer 105 (into hole 150 which does not appear), spool 70 is positioned over soldered joint 115 of the bridgework, and secondary supports 50, 60 are set in close proximity to the position of the spool. The instrument is then set aside.

Figure 9C:
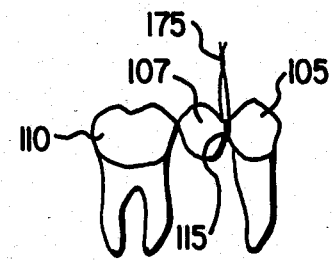

STEP 3: As shown in FIG. 9C, a pulling cord or wire 175 (preferably 0.020 inch dead soft orthodontic ligature wire sometimes double stranded) is then threaded beneath the bridgework under soldered joint 115, and is loosely twisted above the occlusal table. The twisted ends should approximate one another.

Figure 9D:
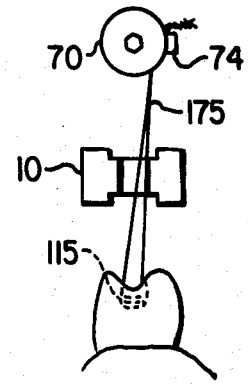

STEP 4: The instrument is again placed in the patient's mouth and, as is shown in FIG. 9D, the ends of the wire 175 are then threaded and engaged with reeling spool 70 through slot opening 74 of the spool. It will be observed in FIG. 9D that wire 175 extends upwardly from beneath soldered joint 115 of the bridgework through an opening of beam 10. The opening may be opening 11 or opening 12 depending upon the position of spool 70 relative to the longitudinal extension of the beam in the case at hand.

STEP 5: With the instrument again positioned as shown in FIG. 9B, but with wire 175 now threaded and loosely engaged with spool 70, shaft 30 is turned slightly such that the spool begins to take up slack and more tightly engage the wire. Shaft 30 should continue to be rotated until there is no longer any slack in the wire. If slippage does occur, it may be necessary in some case to bend the wire over the top of spool 70.

STEP 6: Substantial rotational force is now applied to shaft 30. Initially wire 175 will stretch and distort until it comes under uniform tension. Then, the cement bond of retainer 105 will break as the instrument is forced against the abutment tooth and soldered joint 115 is pulled in an occlusal direction. It should be appreciated that the tightly cemented retainer may be well secured, thus requiring considerable force to break the bond. However, since there is a net balancing of forces on the bridgework, and since the pull is in an occlusal direction, the effect on the patient will usually be minimal.

CASE 2

Figure 10A:
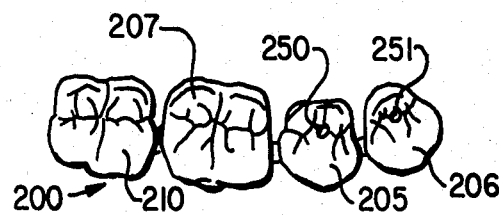
FIGS. 10A and 10B depict different dental bridgework and an example of the use of the instrument of FIG. 1 with an added bracing pin.
Figure 10B:
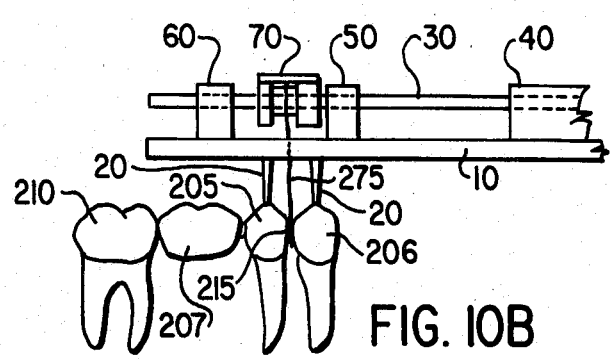

This example, illustrated by FIGS. 10A and 10B involves the removal of adjacent splinted retainers.

Dental bridge 200 of FIGS. 10A and 10B has two retainers 205, 206 which are tightly cemented and one retainer 210 which is loose. A pontic 207 is disposed between retainers 210, 215. The removal of such bridgework for purposes of repair includes the following steps:

STEP 1: As shown in FIG. 10A, small holes 250, 251 are cut into the occlusal surfaces of retainers 205, 206. As in Case 1, such surfaces are sufficiently exposed to just receive lower end 24 of bracing pin 20, and there should be no binding of metal at any time during that procedure.

STEP 2: For purposes of establishing and setting the positions of adjustable components on beam 10, the instrument of FIG. 1, now with two bracing pins 20, is placed in the patient's mouth. The span between pins 20 is measured and set such that one of the pins extends down to retainer 205, and the other down to retainer 206 (into the holes 250, 251 provided in such retainers). Spool 70 is positioned over soldered joint 215 between the retainers, and secondary supports 50, 60 are set in close proximity to the position of the spool.

STEP 3: Similar to Step 3 of Case 1 using double stranded 0.020 inch ligature wire 275 as a pulling cord.

STEP 4: Similar to Step 4 of Case 1, the instrument is again placed in the patient's mouth to the position shown in FIG. 10B. As can be seen, wire 275 extends upwardly from beneath soldered joint 215 of the bridgework.

STEPS 5 and 6: Similar to Steps 5 and 6 of Case 1.

CASE 3

Figure 11A:
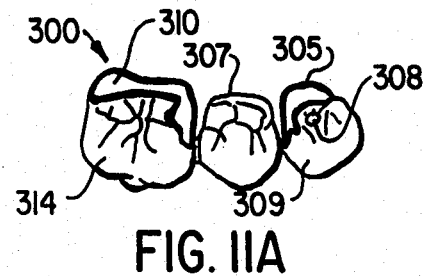
FIGS. 11A and 11B depict a "Maryland Bridge" form of dental bridgework and use of an instrument similar to that shown in FIG. 1, but with certain modifications.
Figure 11B:
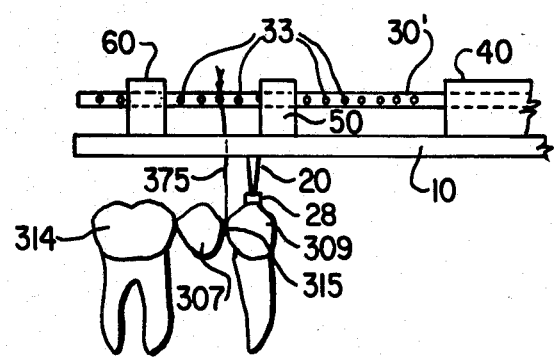

This example, illustrated by FIGS. 11A and 11B, involves the removal of a "Maryland Bridge" generally designated 300. The bridge comprises one retainer 305 tightly cemented, a pontic 307, and one retainer 310 which is loose.

The arrangement appearing in FIG. 11A is similar to that which appears in FIG. 9A with the distinction that FIG. 11A depicts in part the natural surface of teeth (viz. surfaces 309, 314).

In FIG. 11B, shaft 30' with a plurality of spaced apart holes 33 simply serves to illustrate the varied structure of shaft 30 discussed above which does not include a reeling spool 70. Pulling cord 375 looped beneath soldered joint 315 is engaged by one of the holes 33.

The removal procedure for the Maryland Bridge may include the following steps:

STEP 1: The positions of adjustable components are determined and set as in previous cases, with pin 20 set to brace against exposed cusp 308 of natural tooth surface 309. As can be seen, pin 20 now includes protective footing 28 as described above in relation to FIG. 8.

STEP 2: Similar to step 3 of Case 1.

STEP 3: Similar to step 4 of Case 1 with the distinction that wire 375 is threaded through a shaft opening 33 above joint 315.

STEPS 4 and 5: Similar to steps 5 and 6 of Case 1.

It will be appreciated that various modifications could be made to the embodiments of the invention which has been described. Alternate means could be devised for the mounting of components such as bracing pins and supports to the beam, and the structure of the beam could be varied to accommodate such alternate means. Further, and although preferable, it is not considered essential that components such as bracing pins and supports should be slidable or slidably engageable with the beam. In addition, persons skilled in the art will undoubtedly recognize that pulling means other than that shown in the FIG. 1 embodiment could be devised to draw a pulling cord or cords. In this regard, the primary requisite is that the pulling means should draw a pulling cord looped beneath dental bridgework perpendicularly (viz. in an occlusal direction) towards the beam.

Accordingly, the present invention is not limited to the particular embodiments which has been described, and is to be viewed within the spirit and scope of the claims which follow.

I claim:

1. An instrument for removing dental bridgework, comprising:
    (a) a support beam having sufficient longitudinal extension to extend into a patient's mouth over bridgework bonded therein;
    (b) a bracing pin having a upper end mounted to said beam, said bracing pin for holding said beam at said upper end mount at a fixed position away from said bridgework during removal of said bridgework; and,
    (c) pulling means comprises an elongated rotatable shaft supported by said beam for rotatably engaging and drawing a pulling cord looped beneath said bridgework in an occlusal direction towards said beam to break said bond when said beam is braced by said pin.

2. An instrument as defined in claim 1, said bracing pin including a lower end receivable by a receiving hole cut in the occlusal surface of a retainer of said bridgework.

3. An instrument as defined in claim 2, wherein said beam includes at least one opening through which said cord may be extended from said bridgework to said pulling means.

4. An instrument as defined in claim 3, including securing means for tightly mounting the upper end of said pin at a selected position on said beam, said pin securing means being releasable to permit sliding movement of said pin along the longitudinal extension of the beam to another selected position while holding said pin loosely mounted on said beam.

5. An instrument as defined in claim 3, wherein said shaft is rotatably supported by a main bearing support mounted on said beam and by at least one secondary bearing support mounted on said beam.

6. An instrument as defined in claim 5, including securing means for tightly mounting said secondary support at a selected position on said beam, said securing means being releasable to permit sliding movement of said secondary support along the longitudinal extension of said beam to another selected position while holding said secondary support loosely mounted on said beam.

7. An instrument as defined in claim 3, wherein said shaft is rotatably supported by a main bearing support mounted on said beam and by first and second secondary bearing supports mounted on said beam.

8. An instrument as defined in claim 7, including first and second securing means for tightly mounting said first and second secondary supports at selected positions on said beam, said first and second securing means being releasable to permit sliding movement of said secondary support along the longitudinal extension of said beam to other selected positions while holding said secondary support loosely mounted on said beam.

9. An instrument as defined in claim 2, wherein said beam includes an elongated opening disposed along the longitudinal extension of the beam and through which said cord may be extended from said bridgework to said pulling means to be engaged by said pulling means.

10. An instrument as defined in claim 2,3 or 4, including a reeling spool slidably mounted on said shaft for engaging said cord.

11. An instrument as defined in claim 5, 6 or 7 including a reeling spool slidably mounted said shaft for engaging said cord.

12. An instrument as defined in claim 8 or 9, including a reeling spool slidably mounted on said shaft for engaging said cord.

13. An instrument for removing dental bridgework, comprising:
(a) a support beam having sufficient longitudinal extension to extend into a patient's mouth over bridgework bonded therein;
(b) a first bracing pin having an upper end mounted to said beam and a lower end receivable by a receiving hole cut in the occlusal surface of a first retainer of said bridgework;
(c) a second bracing pin having an upper end mounted to said beam and a lower end receivable by a receiving hole cut in the occlusal surface of a second retainer of said bridgework; and,
(d) said first and second bracing pins for holding said beam at said upper end mounts at a fixed position away from said bridgework during removal of said bridgework; and,
(e) pulling means supported by said beam for rotatably engaging and drawing at least one pulling cord looped beneath said bridgework in an occlusal direction towards said beam to break said bond when said beam is braced by said pins.

14. An instrument as defined in claim 13, wherein said pulling means comprises an elongated rotatable shaft for drawing said cord.

15. An instrument as defined in claim 14, wherein said beam includes at least one opening through which said cord may be extended from said bridgework to said pulling means to be engaged by said pulling means.

16. An instrument as defined in claim 15, each pin including securing means for tightly mounting its said upper end at a selected position on said beam, said pin securing means for each pin being releasable to permit sliding movement of the pin along the longitudinal extension of the beam to another selected position while holding the pin loosely mounted on said beam.

17. An instrument as defined in claim 15, wherein said shaft is rotatably supported by a main bearing support mounted on said beam and by at least one secondary bearing support mounted on said beam.

18. An instrument as defined in claim 17, including securing means for tightly mounting said secondary support at a selected position on said beam, said securing means being releasable to permit sliding movement of said secondary support along the longitudinal extension of said beam to another selected position while holding said secondary support loosely mounted on said beam.

19. An instrument as defined in claim 15, wherein said shaft is rotatably supported by a main bearing support mounted on said beam and by first and second secondary bearing supports mounted on said beam.

20. An instrument as defined in claim 19, including first and second securing means for tightly mounting said first and second secondary supports at selected positions on said beam, said said first and second securing means being releasable to permit sliding movement of said secondary support along the longitudinal extension of said beam to other selected position while holding said secondary support loosely mounted on said beam.

21. An instrument as defined in claim 14, wherein said beam includes an elongated opening disposed along the longitudinal extension of the beam and through which said cord may be extended from said bridgework to said pulling means to be engaged by said pulling means.

22. An instrument as defined in claim 14, 15 or 16, including a reeling spool slidably mounted on said shaft for engaging said cord.

23. An instrument as defined in claim 17, 18 or 19, including a reeling spool slidably mounted on said shaft for engaging said cord.

24. An instrument as defined in claim 20 or 21, including a reeling spool slidably mounted on said shaft for engaging said cord.

25. An instrument as defined in claim 2, 3 or 14, wherein said shaft includes a plurality of spaced apart holes for receiving and engaging said cord 26. An instrument as defined in claim 2, 3 or 4 wherein said pin includes a protective footing for bracing against an exposed cusp of a tooth, said footing being removably attachable to said lower end of said bracing pin.

27. An instrument as defined in claim 4, 5 or 6, wherein said shaft includes a plurality of spaced apart holes for receiving said cord, said holes being directed transverse to the longitudinal extension of said shaft.

28. An instrument as defined in claim 1, wherein said bracing pin includes a lower protective footing for bracing against an exposed cusp of a tooth.

29. An instrument as defined in claim 28, wherein said beam includes at least one opening through which said cord may be extended from said bridgework to said pulling means to be engaged by said pulling means.

30. An instrument as defined in claim 29, including securing means for tightly mounting the upper end of said pin at a selected position on said beam, said pin securing means being releasable to permit sliding movement of said pin along the longitudinal extension of the beam to another selected position while holding said pin loosely mounted on said beam.

31. An instrument as defined in claim 28, 29, or 30, wherein said shaft includes a plurality of spaced apart holes for receiving and engaging said cord.

32. An instrument as defined in claim 28, 29 or 30, wherein said protective footing is removably attachable to a lower end of said pin.

* * * * *